United States Patent [19]
Sablotsky et al.

[11] Patent Number: 5,405,486
[45] Date of Patent: Apr. 11, 1995

[54] APPARATUS FOR FORMING A TRANSDERMAL DRUG DEVICE

[75] Inventors: Steven Sablotsky; Ronald E. LaPrade, both of Miami, Fla.

[73] Assignee: Noven Pharmaceuticals, Inc., Miami, Fla.

[21] Appl. No.: 80,223

[22] Filed: Jun. 21, 1993

Related U.S. Application Data

[63] Continuation-in-part of Ser. No. 691,354, Apr. 25, 1991, abandoned, which is a continuation-in-part of Ser. No. 407,874, Sep. 15, 1989, Pat. No. 5,032,207, which is a continuation-in-part of Ser. No. 295,847, Jan. 11, 1989, Pat. No. 4,994,267, which is a continuation-in-part of Ser. No. 164,482, Mar. 4, 1988, Pat. No. 4,814,168.

[51] Int. Cl.⁶ .................................. B32B 31/18
[52] U.S. Cl. .................. 156/510; 156/250; 156/267; 156/268; 156/270; 156/581; 83/861; 83/862
[58] Field of Search ............ 156/248, 250, 257, 261, 156/263, 267, 268, 270, 510, 528, 581; 83/52, 620, 621, 861, 862

[56] References Cited

U.S. PATENT DOCUMENTS

| | | | |
|---|---|---|---|
| 1,357,665 | 11/1920 | Watkins . | |
| 1,441,708 | 1/1923 | Overbury . | |
| 1,963,393 | 1/1934 | Woodall | 154/2 |
| 2,069,049 | 9/1952 | Rayburn | 164/84.5 |
| 3,006,793 | 10/1961 | Wheeler et al. | 154/53.5 |
| 3,120,777 | 2/1964 | Genin | 83/11 |
| 3,340,778 | 9/1967 | Boone et al. | 93/58 |
| 3,347,119 | 10/1967 | Sarka | 83/38 |
| 3,477,625 | 11/1969 | Wiest | 225/96 |
| 3,552,244 | 1/1971 | Smith | 83/9 |
| 3,552,291 | 1/1971 | Feick | 93/58.2 |
| 3,577,889 | 5/1971 | Eriksen | 83/7 |
| 3,749,626 | 7/1973 | Buck | 156/251 |
| 3,786,732 | 1/1974 | Forbes, Jr. | 93/58.3 |
| 3,965,786 | 6/1976 | D'Luhy | 83/346 |
| 3,981,213 | 9/1976 | Lopman | 83/346 |
| 4,016,786 | 4/1977 | Korner | 83/9 |
| 4,080,878 | 3/1978 | Gallagher et al. | 93/58 ST |
| 4,142,455 | 3/1979 | Coburn | 93/58.2 R |
| 4,248,117 | 2/1981 | Bugnone | 83/863 |
| 4,618,342 | 10/1986 | Borel | 493/30 |
| 4,759,247 | 7/1988 | Bell et al. | 83/346 |
| 5,032,207 | 7/1991 | Sablotsky et al. | 156/250 |
| 5,083,488 | 1/1993 | Stanley et al. | 83/344 |

FOREIGN PATENT DOCUMENTS

WO91/17027 11/1991 WIPO .

*Primary Examiner*—Caleb Weston
*Attorney, Agent, or Firm*—Foley & Lardner

[57] ABSTRACT

Disclosed is a method and apparatus for forming a transdermal drug delivery device from a multilayer web comprised of a backing layer, a drug-containing pressure sensitive adhesive layer, and a release layer or liner in which cutting is progressively achieved along a line coplanar with the axes of a cutting roller and anvil roller counter-rotating in proximity to each other. In one embodiment, cutting is achieved completely through the web about the periphery of the transdermal drug delivery device, while simultaneously achieving a scoring only of the release liner without penetration of the pressure sensitive adhesive layer or backing layer. In an alternate embodiment there are two arrangements of rollers. A first arrangement has a cutting edge for scoring the web. After scoring, the web is passed to a second arrangement for cutting through the web to result in the transdermal drug delivery device.

42 Claims, 7 Drawing Sheets

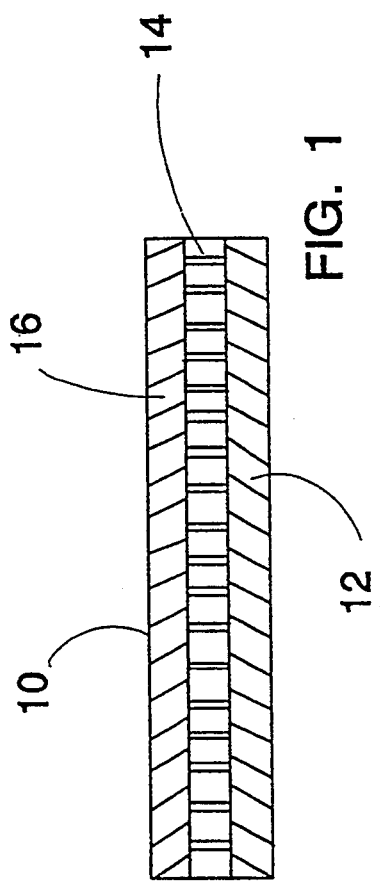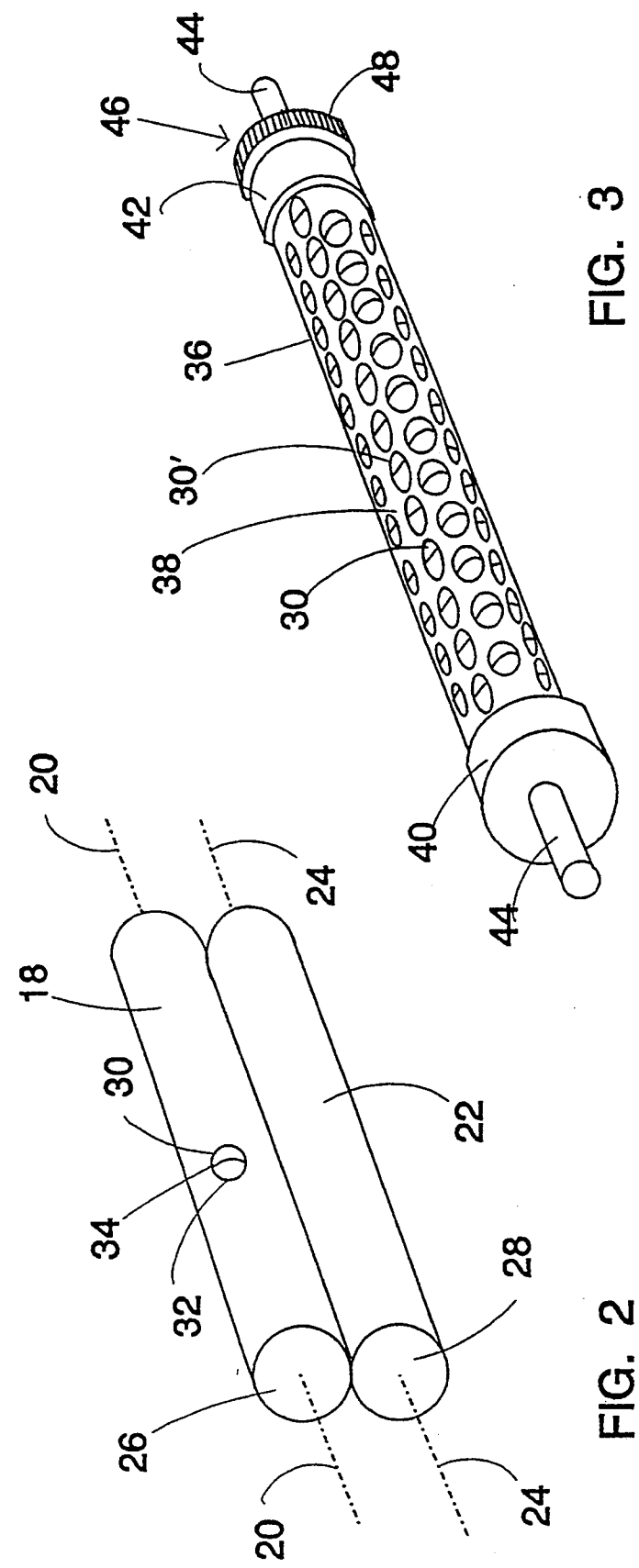

APPARATUS FOR FORMING A TRANSDERMAL DRUG DEVICE

CROSS REFERENCE TO RELATED APPLICATIONS

This application is a continuation-in-part of U.S. patent application Ser. No. 07/691,354, filed Apr. 25, 1991, abandoned, which is a continuation-in-part of U.S. patent application Ser. No. 407,874, filed Sep. 15, 1989, now U.S. Pat. No. 5,032,207, issued Jul. 16, 1991, which was a continuation-in-part of U.S. patent application Ser. No. 295,847, filed Jan. 11, 1989, now U.S. Pat. No. 4,994,267, issued Feb. 19, 1991, which was, in turn, a continuation-in-part of U.S. patent application Ser. No. 164,482, filed Mar. 4, 1988, now U.S. Pat. No. 4,814,168, issued Mar. 21, 1989, all of which applications are hereby incorporated by reference herein.

FIELD OF THE INVENTION

The present invention relates to the field of manufacture of medical devices for the administration of a drug through the skin of a patient, and more particularly relates to a method and apparatus for the formation of such an article of manufacture having a layered laminate structure comprised of a backing layer, a drug-containing pressure sensitive adhesive layer, and a release layer or liner.

BACKGROUND OF THE INVENTION

For some time now, it has been known by the medical profession that certain drugs may be administered to patients by being absorbed over a period of time directly through the epidermis or skin of the patient without using a hypodermic syringe or other invasive technique. Drugs that are intended to be administered in this manner may be compounded in a matrix of other materials suitable for contact with the skin of the patient. One technique for doing so is to combine the drug to be administered transdermally with a pressure sensitive adhesive which can be firmly attached to the skin in a manner which will assure excellent contact with the skin and allow migration of the drug from the pressure sensitive adhesive transdermally to the body of the patient. When this technique is employed, the structure of the article of manufacture includes a backing to protect the pressure sensitive adhesive from contact with other objects and to prevent loss of the drug. Also included is a release liner which is to be removed from the pressure sensitive adhesive immediately prior to application thereof to the skin of the patient. The structure of such transdermal drug delivery devices is shown and described in our application Ser. No. 407,874, now U.S. Pat. No. 5,032,207, issued Jul. 16, 1991.

In order to facilitate practical and economical manufacture and use of such a transdermal device, it has been found useful to score the release liner so as to permit said liner to be easily removed from the adhesive carrying drug in one step. Our prior related applications describe various techniques and apparatus to accomplish this objective of scoring the liner to permit said liner to be easily removed from the drug-containing pressure sensitive adhesive. However, continuing development for improved manufacturing efficiency and operational considerations has resulted in improvements and variations to that described in the earlier cross-referenced applications. Accordingly, this application is directed to a reflection of those improvements.

Several apparatus and methods are believed to have been devised for intermittently or continuously scoring the release liner portion of a transdermal drug delivery device in order to permit said liner to be easily removed from the drug-containing pressure sensitive adhesive disposed between the release liner and the backing in such devices. The liner is, of course, removed from the device immediately prior to its being applied to the skin on the patient. The typical procedure for the preparation of a transdermal drug delivery device involves a plurality of steps. First, a dilution or suspension of the adhesive is compounded with an appropriate concentration of the drug and is applied to a flexible layer intended to function as a disposable release liner, frequently made of plastic. This release liner also forms, during processing, the means to carry a pressure sensitive drug-containing adhesive through the manufacturing and cutting operation thereafter. Next, a non-releasable or primed backing material is applied over the adhesive. The result is a laminate in the form of a web containing an adhesive with a backing on one side and a disposable release liner on the other side. A shaped and precisely sized device is then formed by peripheral cutting through all the layers of the resulting web. The disposable release liner can then be removed and a second, scored release liner can be attached to the transdermal drug-containing adhesive.

Alternatively, the liner can be first scored and assembled with the adhesive and the backing and then the laminate web cut to the desired dimensions.

The purpose of the multi-step procedure for applying the backing and the release liner to the adhesive containing the drug is to avoid problems encountered when a scored release liner is used in processing. If a completely cut release liner is used prior to coating, the drug-containing adhesive can pass through the release liner at the score causing equipment problems, cracking, separation, heat damage, loss of raw materials, and possible exposure of factory workers to the drug or similar environmental concerns.

Moreover, these prior art methods suffer from the disadvantage that the procedure for applying the release liner requires several steps, and thus have a tendency to be more expensive in mass production than a procedure which involves fewer steps.

In one aspect, the present invention overcomes the difficulties and disadvantages associated with prior art devices by providing a method and apparatus for simultaneously cutting an assembled transdermal drug delivery device from a web comprising a backing layer, a drug-containing pressure sensitive adhesive and a release liner while at the same time scoring the release liner at a position intermediate to the periphery of the transdermal drug delivery device.

In another aspect, the present invention overcomes the difficulties and disadvantages associated with prior art devices by providing a method and apparatus for sequentially first scoring the release liner of an assembled transdermal drug delivery device from a web comprising a backing layer, a drug-containing pressure sensitive adhesive and a release liner, and thereafter cutting the transdermal drug delivery device from the web.

Accomplishing the objectives of this invention is achieved, in part, by providing two types of cutting edges, one sized to cut completely through the periphery of the laminate web to size and form the transdermal drug delivery devices, and a second type sized to only cut or score the release liner at a position intermediate to the periphery, and which intermediate or center scoring does not extend all the way to the adhesive nor to the non-releasable backing. These advantages are accomplished by the use of the first type of cutting edges having the configuration and size of the transdermal drug delivery device to be cut from the web which cutting edges are sufficient in dimension to cut completely through the web and thus through the backing, adhesive, and release liner layers. At the same time, the second type or intermediate or center portion cutting edge is sized to score the release liner to a point just short of the adhesive liner or through the release layer, but not to the adhesive.

There are, of course, prior art devices which relate to apparatuses for scoring or cutting material in the form of a sheet, even when the same is formed from a laminated product. For example, Forbes, Jr., U.S. Pat. No. 3,786,732, relates to an apparatus for scoring a sheet like material. However, it refers to the scoring of carton blank material. The material thereby scored, is substantially different from a pressure sensitive adhesive containing laminate having a degree of dimensional instability and less resistance to cutting action. It is recognized that the apparatus of Forbes, Jr. does not teach a formation for cutting of a drug-containing pressure sensitive adhesive sandwiched between a backing layer and a release liner.

Another prior art reference is Woodall, U.S. Pat. No. 1,963,393, which relates to the cutting of a laminated panel, particularly for a sun visor, to protect automobile drivers. The disclosure relates a panel formed of a sheet of thermal plastic material, which has a fabric on one side attached by an adhesive.

However, both of these references constitute non-analogous prior art, because one skilled in the art attempting to construct a nearly paper-thin transdermal drug delivery device, substantially in the form of a bandage, and having a dimensionally unstable cross-section, would not expect to look for guidance in the arts of cutting and scoring laminated panels or sheet materials. The laminate of the subject transdermal drug delivery device includes one relatively hard surface, i.e., the release liner, a soft or flexible surface, i.e., the backing layer, and a dimensionally unstable inner layer, i.e., the drug-containing pressure sensitive adhesive.

SUMMARY OF THE INVENTION

Bearing in mind the foregoing, it is a principal object of the present invention to provide an apparatus that will, with a singular mechanical motion accomplish the purposes of moving a laminate web comprising a backing layer, a drug-containing pressure sensitive adhesive layer, and a release liner through a sizing operation, while at the same time at least one of cutting a periphery of a transdermal drug delivery device to thereby size and shape said device from the laminate web and scoring the release liner of said device to a precise degree sufficient to facilitate easy removal of that liner from the drug-containing pressure sensitive adhesive layer. The scoring is done in such a manner as to avoid cutting the release liner to a degree which will allow adhesive or any volatile solvent contained therein to pass through the liner and thereby escape prematurely from the transdermal drug delivery device.

A further principal object of the invention is to provide in one aspect a single step method which causes movement of the laminate web from which a transdermal drug delivery device is to be formed, while at the same time forming said device to a predetermined size and shape, while at the same time scoring the layer of said device used as a disposable release liner to a precise degree in a manner which will avoid premature release of the drug-containing adhesive, any volatile solvent or the drug itself.

A further principal object of the invention is to provide in another aspect a two step method which causes movement of the laminate web from which a transdermal drug delivery device is to be formed while initially scoring the layer of said device used as a disposable release liner to a precise degree in a manner which will avoid premature release of the drug-containing adhesive, any volatile solvent or the drug itself, and sequentially forming the device to a predetermined size and shape.

Another object of the invention is to incorporate the foregoing objectives utilizing a rotary motion capable of continuous, precisely controlled and economical motion that is appropriate for efficient mass production of transdermal drug delivery devices.

Yet another object is to achieve the cutting and scoring in a manner wherein the web is supported fully in a manner so as to avoid flexing and resulting imprecision in scoring and cutting.

An additional object of the invention is to achieve the aforementioned cutting action along a line disposed between the rotating cylindrical members positively rotating at the same angular speed, resulting in cutting force being asserted in a substantially linear and precise manner, rather than being distributed across the entire periphery and intermediate (or center) in a less precisely controlled manner requiring greater force because all points are substantially simultaneously cut.

A related object of the invention is to achieve the foregoing objects and advantages with an apparatus and method which avoids stopping and starting that is inherent in apparatus and methods which reciprocate, as is required in our prior invention disclosed in the cross-referenced related applications.

A collateral object of the invention is to reduce the unit manufacturing cost of transdermal drug delivery devices by utilizing rotating machinery, as opposed to reciprocating machinery to achieve higher production rates, less maintenance down time, and consequent lower maintenance cost such as typically results from replacement of reciprocating machinery with rotating machinery.

A further object of the invention is to position the cutting edges about the circumference of a cylinder or roller while at the same time sizing the diameter of the cylinder such that a plurality of transdermal drug delivery devices can be cut from a moving laminate web in close packed arrangement and with a repeat length caused by prior sizing of cylinder diameter to minimize waste in the web from which the transdermal drug delivery devices are cut using the inventive apparatus and method. This positioning of the cutting edges about the circumference of the cylinder is such as to close pack the positioning to minimize waste of the web between the location of the transdermal drug delivery devices removed therefrom to achieve minimum waste and the greatest possible manufacturing economies.

Other objects and advantages will be apparent to those skilled in the art upon reference to the following descriptions and the drawings.

In accordance with a major aspect of the invention, there is provided an apparatus including at least one arrangement of plurality of cylinders in proximity to each other and disposed such that the axis of each is coplanar with the axis of the other. Each such cylinder is rotationally mounted in bearing means and supported thereby in a framework that permits the distance or pressure between the axes of the cylinders to be controlled. On at least one of these cylinders, referred to as the cutting cylinder or roller, are disposed at least one type of cutting edges. The one type of cutting edges can be of one of two types. One type is shaped to cut and size the laminate web entirely therethrough to form the transdermal drug delivery device from the laminate web. Another type is shaped and used to score the release liner without affecting the drug-containing pressure sensitive adhesive adjoining the release liner, nor the backing layer adjoining the drug-containing pressure sensitive adhesive. The other cylinder is disposed and positioned in a manner proximal the cutting cylinder. The two cylinders are simultaneously driven to achieve substantially identical surface speed and in such proximity as to just permit the laminate web to pass therethrough as said cylinders rotate on their axes. Cutting action between these cylinders is achieved as said laminate web passes through the plane of the axes of both cylinders.

In one aspect both cutting and scoring edges are arranged on a single cutting cylinder in a single arrangement of cylinders so as to have the laminate web passed through the plane of the axes of both cylinders, simultaneously intersecting the peripheral cutting edges and the release liner scoring edge at the points at which each of said edges are disposed on the surface of the cutting cylinder and pass through the plane of the cylinder axes, thus achieving the linear cutting action above-described.

In accordance with another major aspect of the invention there are two arrangements of cylinders disposed for sequential passage of the laminate web through the first arrangement for scoring the laminate web which is then passed to a second arrangement for cutting the laminate web. In this case, the cutting roller in the first arrangement of cylinders has only the scoring edges thereon and the cutting roller in the second arrangement of cylinders has the cutting edges thereon.

In accordance with both noted aspects of the invention, there is provided for each arrangement of cylinders an apparatus comprising a rigid support means having a surface in the form of a first cylinder. This support cylinder has an axis and rotatably mounted on that axis is a shaft which, in turn, is mounted in bearing means, said bearing means being disposed within a framework. The support cylinder is later referred to as an anvil roller.

At least one cutting means is fixedly mounted on a second cylinder having an axis and a shaft coaxial therewith and also being rotatably mounted within bearing means. Said bearing means is disposed within a frame such that the axis of the first or support cylinder (anvil roller) and the axis of the cutting cylinder (cutting roller) are coplanar, with at least one pair of said bearing means being controllably movable with respect to a second pair of said bearing means to controllably vary the distance and/or pressure between the axes of the anvil roller and the cutting roller.

The at least one cutting means fixedly mounted on a surface of the cutting roller has at least one cutting edge extending outwardly from a surface of the cutting roller for a first predetermined distance. Said cutting edge is configured as a closed loop mounted on and projected above the surface of the cutting roller in a predetermined shape for defining a first region of the cutting roller surface.

Optionally, at least another cutting means is fixedly mounted on and projected above the surface of the same cutting roller having said at least one cutting means within said first region, said another cutting means having a cutting edge extending outwardly from the cutting roller for a second predetermined distance, said second predetermined distance being less than said first predetermined distance, said second cutting means dividing said first region of the cutting cylinder surface to form first and second sub-regions thereof.

Alternatively, two arrangements of rollers are provided for passing the web between the two arrangements. In sequence of passage, the first arrangement has a cutting roller having only said another cutting means thereon. The second arrangement has only said one cutting means thereon.

A multilayered laminate web means includes a first layer of release liner, a second layer of a drug-containing pressure sensitive adhesive adhering to said release liner, and a third layer forming a backing adhering to the drug-containing pressure sensitive adhesive layer. Said laminate multilayered web is urged first layer first into communication with said one and another cutting means. The one cutting means is arranged to communicate with and penetrate through said first, second and third layers of said multilayered laminate web means, and said another cutting means is arranged to communicate with said first layer release liner only. Said urging is through the counter-rotation of the support cylinder and cutting cylinder in proximity to each other.

In accordance with another aspect of the invention there is provided a method in which a multilayered laminate web is urged between a pair of counter-rotating cylinders rotatably mounted in bearing means in proximity to each other, said multilayered laminate web being urged by said counter-rotation into a gap formed between a support cylinder and a cutting cylinder to achieve a cutting action of said multilayered laminate web along a line between the pair of cylinders and coplanar with the axis of both cylinders, with the method of cutting being established by at least one cutting means fixedly mounted and projected on the surface of a cutting cylinder, said first cutting means having a cutting edge extending outwardly from the cutting cylinder surface for a first predetermined distance. The cutting edge is configured as a closed loop in a predetermined shape for defining one region projected on the cutting cylinder surface. Optionally, the same cylinder has another cutting edge fixedly mounted and projected on the cutting cylinder edge within said first region, said another cutting means having an edge portion extending outwardly from said cutting cylinder edge for a second predetermined distance. The second predetermined distance is less than said first predetermined distance, and said another cutting means divides said first region of said support cutting cylinder edge to form first and second sub-regions thereof. The laminate multilayered web means is formed of a first layer release liner, a second layer formed of a drug-containing pressure sensitive adhesive adhering to said first layer, and a third layer formed of a backing adhering to said second layer. The multilayered laminate web means is urged by the counter-rotation of the cylinders in proximity to each other into communication with one and another cutting means. The one cutting means is arranged to communicate with and penetrate through said first, second and third layers of said multilayered laminate web means, and said another cutting means is arranged to communicate with said first layer only.

Alternatively, the web is passed through a first arrangement of rollers wherein the cutting roller has only said another cutting means for scoring. From said first arrangement of rollers, the web is then passed to a second arrangement of rollers wherein the cutting roller has only said one cutting means for cutting all the way through the web to result in the transdermal drug delivery device.

The invention will be better understood upon reference to the drawings and detailed descriptions thereof which follow, and which:

BRIEF DESCRIPTION OF THE DRAWINGS

FIG. 1 is a cross sectional view of a transdermal drug delivery device showing its multilayer laminate structure.

FIG. 2 is a perspective view showing the apparatus of the invention in its simplest form, on which only one cutting section is shown to form a single transdermal device.

FIG. 3 is a perspective view of a cutting roller showing a close packed arrangement of cutting sections over substantially the entire surface of the roller and also showing pressure journals, drive gear, and shaft ends.

DETAILED DESCRIPTION OF PREFERRED EMBODIMENT

Figure 4:
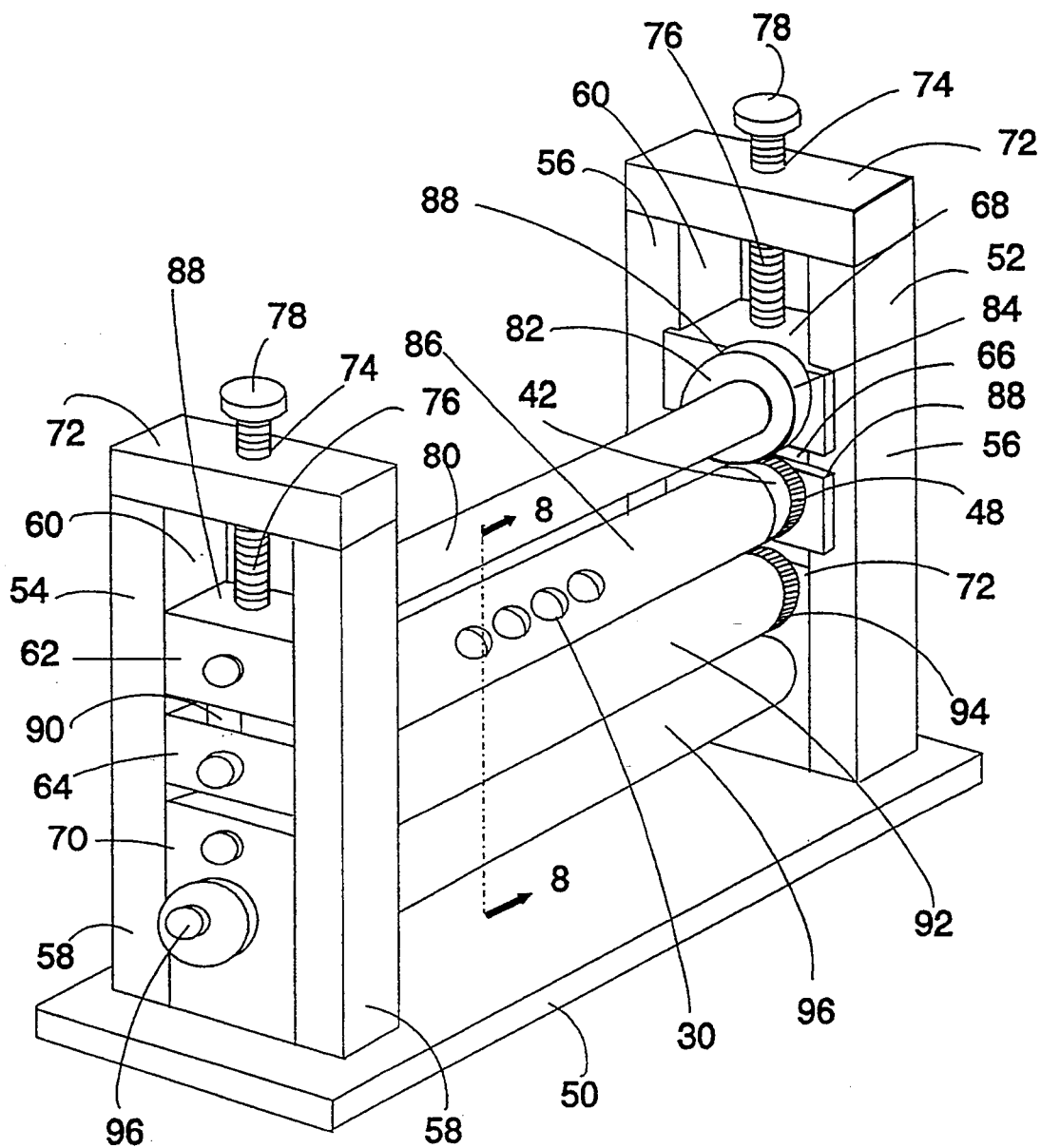
FIG. 4 is a perspective view of a stack in which the pair of rollers shown in FIG. 2 are centrally disposed between a lower rubber covered nip roller, and an upper pressure roller.

FIG. 1 is a cross section view of the laminate multilayer transdermal drug delivery device 10 and also the web material from which it is formed by the present invention. The laminate web or transdermal device 10 is comprised of a release liner 12, a drug-containing pressure sensitive adhesive layer 14, and a back layer 16.

FIG. 2 shows one embodiment of the invention in perspective view with a cutting roller 18 which rotates on axis 20 and an anvil roller 22 which rotates on axis 24. When viewed from left end faces 26 and 28, cutting roller 18 may, for example, rotate on axis 20 counterclockwise and then anvil roller 22 will rotate on axis 24 clockwise. They will preferably be driven together positively so as to operate with the same surface speed. Also shown in FIG. 2 is a cutting section 30 having a peripheral cutting edge 32 and a center cutting edge 34.

FIG. 3 illustrates one preferred embodiment of a cutting roller such as 18, except that this cutting roller 36 has the maximum number of cutting sections 30 disposed on its face in a close packed arrangement so as to minimize the losses resulting from scrap. All of the material in web 10 from which the transdermal devices are cut disposed between cutting sections 30 and 30' as shown at 38 constitutes scrap, which scrap necessarily includes not only backing material, release liner, and pressure sensitive adhesive, but also the drug for which the transdermal device formed by the present invention is to be used, which drug may be expensive. Accordingly, the preferred embodiment of the cutting roller shown in FIG. 3 is to minimize scrap. The cutting roller of FIG. 3 is also shown with pressure journals 40 and 42. The purpose of these journals is illustrated in FIG. 4. Also shown are shaft ends 44 which are preferably disposed within bearing blocks hereinafter illustrated for rotational support and positioning within an operating framework as hereinafter shown and described. On the drive end 46 of cutting roller 36 is also shown a driving means such as a spur gear 48 which meshes with similar driving means such as anvil roller spur gear similarly disposed for a positive drive therebetween, as illustrated in FIG. 4.

FIG. 4 illustrates in perspective view the apparatus of the present invention through which the inventive method is practiced. Shown therein is a base 50 on which are mounted drive side frame 52 and operator side frame 54. Vertical columns 56 of drive side frame 52 and 58 of operator side frame 54 all contain precision machined interior surfaces 60 for slidable engagement of bearing blocks 62, 64, 66, and 68. Anvil roller bearing blocks 70 and 72 are not slidable. Drive side frame 52 and operator side frame 54 both contain a top 72 centrally perforated by a threaded hole 74 through which is disposed a threaded pressure applicator 76 which is rotated for that purpose using knurled knob 78. Rotationally disposed between bearing block 68 and bearing block 62 and 68, is pressure roller 80 which contains symmetrically at both ends, a pressure journal 82 having a precision machined circumference 84. Disposed between bearing blocks 64 and 66 is cutting roller 86 on which can be seen pressure journal 42 and spur gear 48. Also shown are a plurality of cutting sections 30.

Before leaving the combination of the pressure roller 80 and cutting roller 86, it is well to examine several other features. Frame 52 retains lips 88 which ride over the inside surfaces of vertical columns 56 thereby restraining bearing blocks within drive side frame 52 notwithstanding their vertical movement. These lips 88 are also found in symmetrical form on bearing blocks 62 and 64 in the internal sides of operator's side frame 54. The pattern is symmetrical with that shown for the drive side and need not, therefore, be separately shown. Another aspect of the relationship between pressure roller 80 and cutting roller 86 is the existence of an optional strain gauge 90 as shown between bearing block 62 and bearing block 64 on the operator's side. A companion strain gauge is also employed on the drive side in symmetrical form, and strain gauges 90 cooperate with conventional electronic equipment to permit reproducibility of the pressure applied to cutting roller 86 by pressure roller 80.

Rotationally supported between bearing blocks 70 and 72 is anvil roller 92 which cooperates with the cutting edges of cutting sections 30 to size and form the transdermal drug delivery devices. Anvil roller 92 includes, on the drive end, spur gear 94 which interconnects with cutting roller spur gear 48 to achieve a positive drive between anvil roller 92 and cutting roller 86. It is anvil roller 92 which is preferably driven by mechanical means connected to its drive shaft that penetrates bearing block 72, but the drive means is conventional and not shown. The entire circumference of anvil roller 92 is preferably precision machined, but this is particularly important at the ends because of contact with pressure journal 42 on the drive side and a symmetrical pressure journal 40 not visible in FIG. 4, but readily seen in FIG. 3. Pressure journals 42 and 40 establish a precise minimum spacing between anvil roller 92 and the cutting edges of cutting sections 30 on the surface of cutting roller 86.

The bottom roller in this stack is a nip roller 96 preferably covered with a resilient material, and most preferably covered with rubber, which is not driven, except by contact with or pressure communicated from anvil roller 92. It is brought into contact by an adjusting mechanism which may optionally be eccentric 96, which is symmetrically provided at both the operator's side frame 54 as illustrated in FIG. 4, and also at drive side frame 52. The combination of anvil roller 92 and rubber nip roller 96 feed the laminate layered web of FIG. 1 into the previously described combination to achieve the inventive method using the inventive apparatus.

Figure 5:
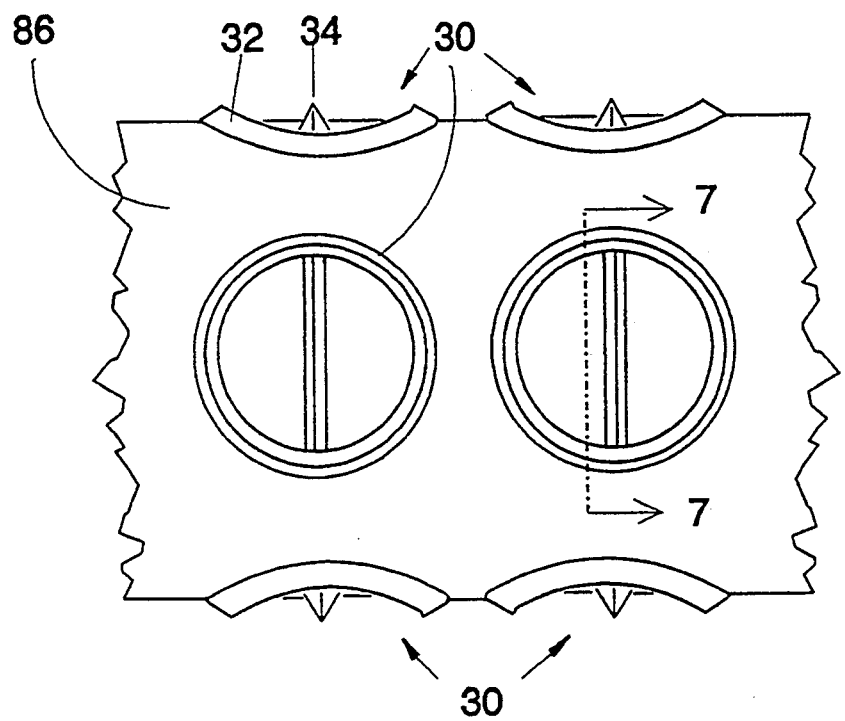
FIG. 5 is a broken slightly enlarged view showing cutting sections at the top, side and bottom of the cutting roller.

Turning now to FIG. 5, a broken front elevation view of cutting roller 86 is shown in a slightly enlarged view with cutting sections 30 at the top and bottom of the roller and also on the side facing the viewer. As briefly described in regard to FIG. 2, cutting sections 30 are comprised of a peripheral cutting edge 32 and an intermediate or center cutting edge 34. Peripheral cutting edge 32 is shown to wrap around the circumference of the roller in this figure. Although the dimensions are more fully described hereinafter, and cannot be readily seen with the degree of enlargement shown in FIG. 5, it should be understood that peripheral cutting edge 32 is intended to cut entirely through release layer 12, drug-containing pressure sensitive layer 14, and backing layer 16 as illustrated in FIG. 1, while center cutting edge 34 is intended to score or out release liner 12 without entering drug-containing pressure sensitive adhesive layer 14 or backing layer 16. The technology for doing so in a planar format is described in our parent application Ser. No. 407,874, now U.S. Pat. No. 5,032,027, which is incorporated herein by reference.

Although the method and apparatus of this invention can be used with release liners that are less flexible, more flexible, or equally flexible as the combination of the backing and drug-containing pressure sensitive adhesive layers, it is desirable to use a backing having the same order of frangibility as the release liner, so that the force needed to cut the entire device, and at the same time score only the release liner, is about the same.

It is important to understand that the present invention represents several improvements over similar technology that is the subject of our prior application Ser. No. 407,874, now U.S. Pat. No. 5,032,027, which employed similar dimensional technology in a planar, reciprocating, total cut at one time, separately fed technique. As an improvement thereon, the present inventive method and apparatus achieves cutting essentially along a line representing the closest point between the cutting edges of cutting sections 30 of cutting roller 86 as seen in FIG. 4 and the surface of anvil roller 92. Thus, as a given cutting section 30 translates by rotation of cutting roller 86 past the aforedescribed line, cutting takes place progressively around the circumference of a given transdermal drug delivery device as the same translates through the closest proximity between the anvil roller and the cutting roller. Moreover, this motion also feeds the web at precisely the right speed to achieve a quality cut with maximum efficiency. The same also results in a continuous rotary motion thereby eliminating reciprocating motion which is inefficient, maintenance prone, slow, and less subject to uniformity.

Figure 6:
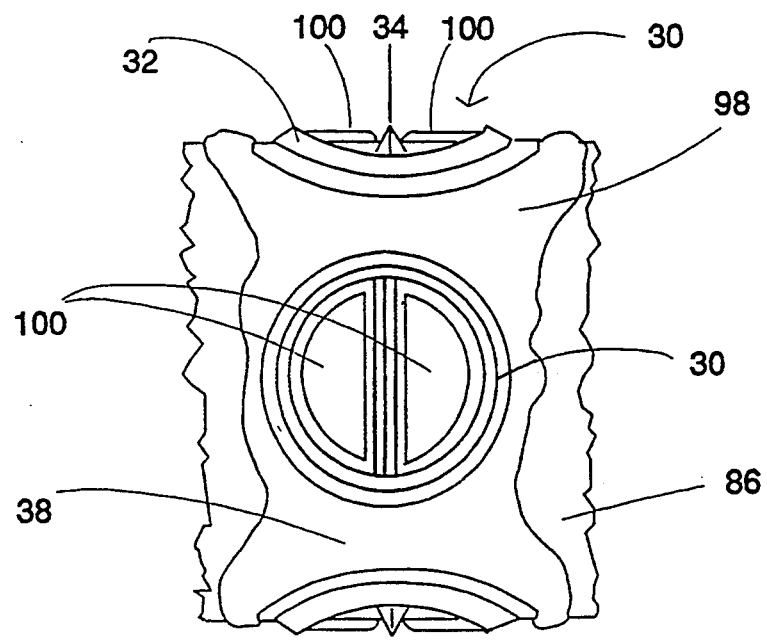
FIG. 6 is an alternative embodiment of half of FIG. 5 which employs a field of resilient material around the cutting sections to discharge the transdermal devices and scrap from the cutting roller after the transdermal device formation has occurred.

FIG. 6 shows an alternative embodiment to that shown in the previous figures in which the cutting sections 30 are surrounded by a layer of highly resilient material, such as a foam rubber 98. Foam rubber 98 will be seen not only to surround the peripheral cutting edge 32, but is disposed on either side of center cutting edge 34 as shown at 100. The resilient material 98 and 100 is intended to achieve rapid discharge of the cut transdermal devices from cutting roller 86 as well as the scrap left after cutting as shown at 38 in this figure, and in FIG. 2. The choice of whether or not to use the resilient material 98 depends on the depth of the web cut. Clearly if the web is very thick, then use of the material 98 is preferred for assisting in the discharge of the cut transdermal devices.

Figure 7:
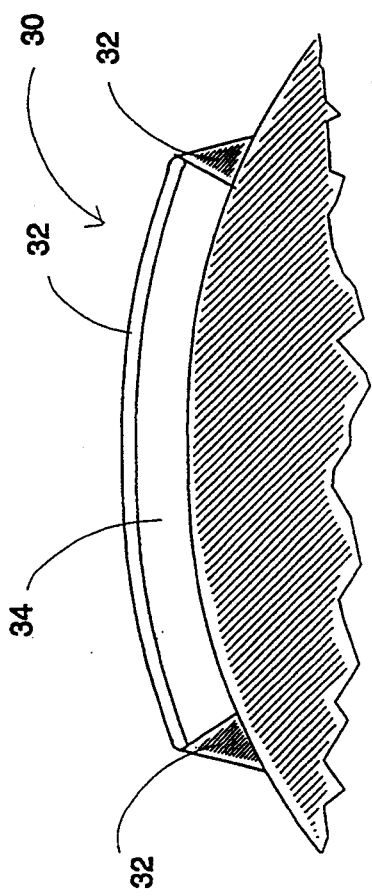
FIG. 7 is a greatly enlarged broken cross sectional view taken along the line 7—7 of FIG. 5 and showing the detail of construction of a cutting section.

FIG. 7 is a greatly enlarged cross sectional view of cutting section 30 taken along the line 7—7 of FIG. 5. It shows that, contrary to the disclosure of our parent application Ser. No. 407,874, now U.S. Pat. No. 5,032,207, the peripheral cutting edge 32 is in the form of an inverted V. That is also the configuration of center cutting edge 34 as illustrated in FIGS. 5 and 6. The difference in height between peripheral cutting edge 34 and center cutting edge 32, which has a shorter dimension is clearly shown by the great enlargement of FIG. 7. Specifically, the peripheral cutting edge 32 generally has a circumference of from 3 to 40 mm and preferably from 7.9 to 17.7 mm depending on the surface area appropriate for delivery of the drug. It has a radius of 0.48 to 6.4 mm, and preferably 1.3 to 2.8 mm, again depending on the appropriate radius for the drug to be delivered, as is known to those skilled in the art.

As stated above, peripheral cutting edge 32 is sized, in cooperation with the thickness of the web shown in FIG. 1 to pass completely through the web, thus cutting through the release liner 12, drug-containing pressure sensitive adhesive layer 14, and backing material 16. Contrariwise, center cutting edge 34 scores the release liner 12 and does not penetrate drug-containing pressure sensitive adhesive layer 14 or backing liner 16. By way of illustration and in general, and without limitation, cutting edge 32 is preferably from 100 to 1,500 microns in height from the base surface of cutting roller 86, and more preferably 900 to 1,000 microns, and even more preferably 930 to 950 microns, although obviously the height of the cutting edge is dependent on the thickness of the web.

Similarly, center cutting edge 34 is preferably 100 to 1,500 microns, and more preferably 850 to 950 microns, and even more preferably 925 to 945 microns, although again the height is totally dependent on the thickness of the release liner. For example, with a web of 10 microns in thickness where the release liner is 6 microns in thickness, cutting edge 32 would be 937 microns in height, while center cutting edge 34 would be 935 microns in height. That is, center cutting edge 34 has to extend sufficiently into the release liner to cause a score, but not sufficiently to cut the drug-containing pressure sensitive adhesive layer.

Figure 8:
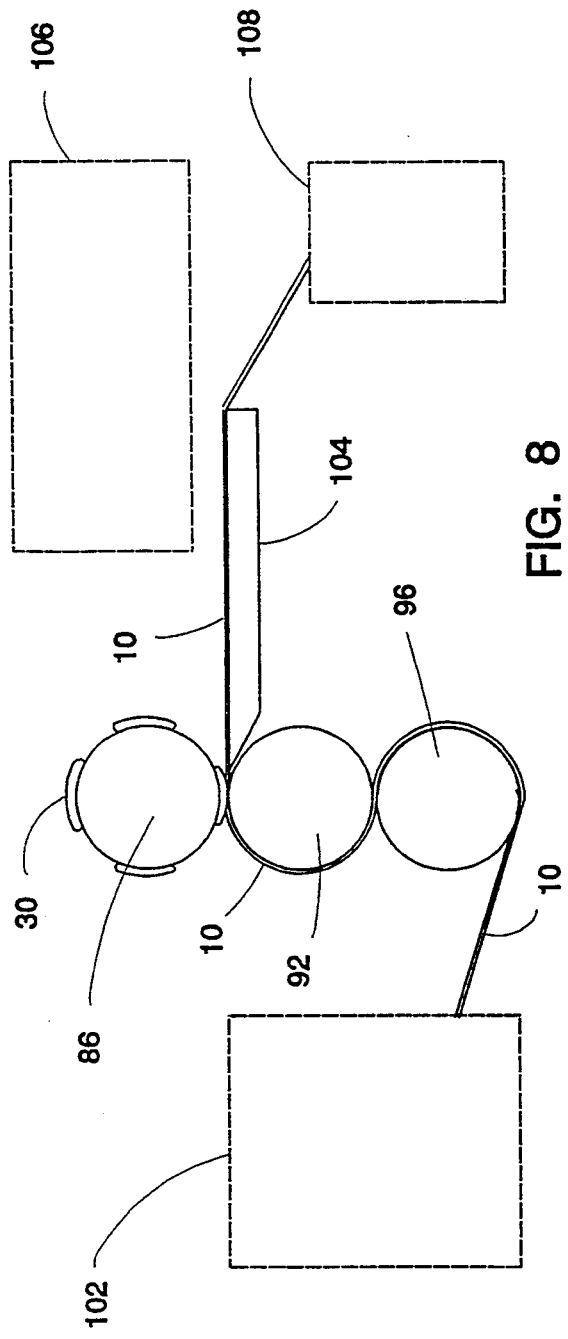
FIG. 8 shows the flow path of a laminate web through one embodiment of the invention. Conventional unwinding, scrap disposal, and proprietary transdermal device pick-up and packaging equipment are shown only generally since they are not a part of the present invention.

Turning now to FIG. 8, a schematic is shown of the web path by which the inventive method and apparatus operates. A quantity or stock of a laminate multilayer web as shown in FIG. 1, preferably in rolled form, is provided to the inventive apparatus and method and unwound using conventional technology as shown at 102. The web 10 enters the stack of rollers beneath a lower rubber covered nip roller 96 whose speed is derived by contact with or pressure transmitted from anvil roller 92. The rotational speed and diameter of nip roller 96 sets the web 10 speed into exact conformity with a continuous rotary motion cutting that occurs thereafter. That is, the speed of web 10 is achieved by contact with rubber covered nip roller 96, in contact and combination with the speed of anvil roller 92. Web 10 then travels from between the nip formed by rubber covered nip roller 96 and anvil roller 92 around to the top of anvil roller 92 to enter into the cutting method and apparatus as occurs between cutting roller 86 and anvil roller 92 as hereinabove described. After cutting takes place, the web 10 is now comprised of scrap material surrounding each of the cutting sections 30 and the transdermal devices which maintain momentarily their position within web 10. Web 10 then travels across a transfer plate 104, which is perforated to prevent the buildup of adhesion or static electricity. The transdermal drug delivery devices are then removed from the web and packaged for storage, shipment, sale, and use, using equipment generally described for that purpose at 106. The same is not shown, described, or claimed in the present application as not constituting part of the present invention although it is proprietary. The remainder of web 10 constituting scrap is then continuously fed to waste disposal 108, of conventional means.

Figure 9:
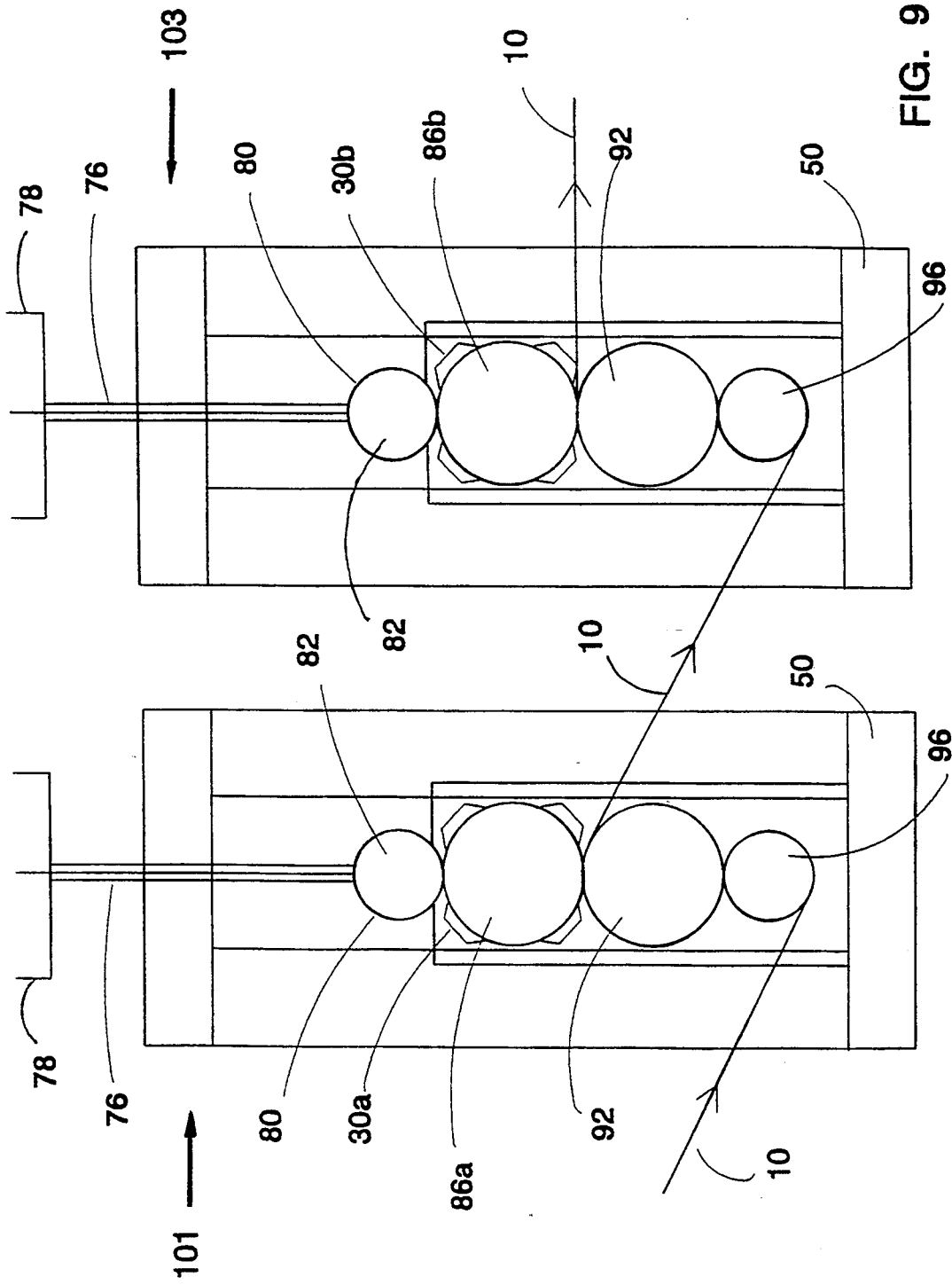
FIG. 9 shows the flow path of a laminate web through an alternate embodiment of the invention similar to FIG. 8, but with two sequential arrangements of rollers, a first arrangement for scoring and a second arrangement for cutting.
Figure 10:
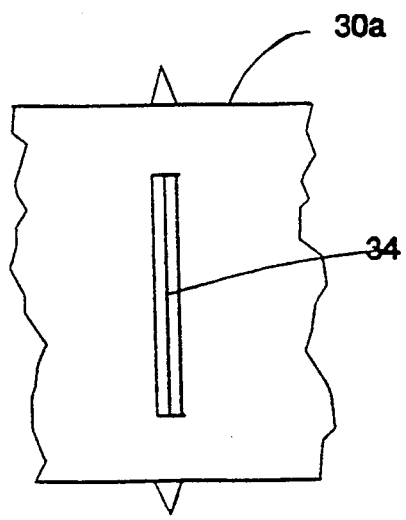
FIG. 10 is a view as in FIG. 5 showing the cutting sections on cutting roller 86a of FIG. 9.

Turning finally to FIGS. 9–10, an alternative apparatus and method in accordance with the invention is illustrated. Specifically, instead of simultaneously scoring and cutting the web 10, the web 10 is first passed through a first assembly of rollers 101 as is shown in FIG. 4. In this embodiment however, a first alternate cutting roller 86a is provided with cutting sections 30a each having scoring cutting edge 34, as shown in FIG. 10, which is preferably the same as cutting edge 34 for the embodiment of FIGS. 2–7.

As shown, the laminate web 10 is first passed underneath nip roller 96 of the first roller assembly 101 and around anvil roller 92 in an S configuration fully supported and backed by the anvil roller 92. The scoring cutting edge 34 of cutting section 30a is designed to cut through the release liner and not through the backing. This is accomplished by providing a clearance between the anvil roller 92 and the cutting edge 34 equal to the thickness of the backing of the laminate of the web 10. Pressure is maintained on the cutting roller 86a and consequently on the cutting edge 34 with pressure roller 80 through pressure applicators 76.

Figure 11:
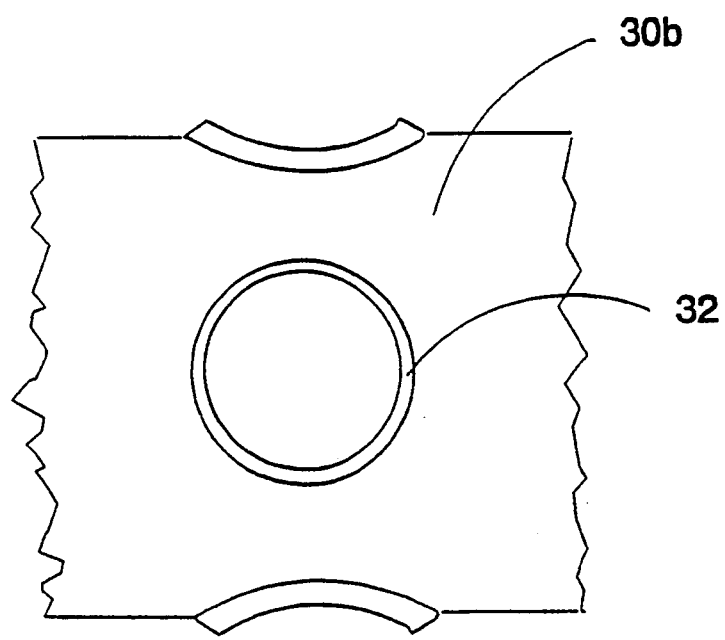
FIG. 11 is a view as in FIG. 5 showing the cutting sections on cutting roller 86b of FIG. 9.

The scored laminate web 10 is then fed from the anvil roller 92 in the first roller assembly 101 to a second roller assembly 103 to nip roller 96 thereof. The web 10 passes in an S configuration, as before, around anvil roller 92 toward cutting roller 86b. The cutting roller 86b in this embodiment has a cutting section 30b with a cutting edge 32 as shown in FIG. 11. The cutting edge 32 is configured to cut completely through the web 10 to result in a scored transdermal drug delivery device of predetermined shape.

To achieve the cutting, pressure is maintained on the cutting edge 32 through the pressure roller 80 with pressure journals 82 by means of the pressure applicators 76 which force the pressure roller 80 down onto cutting roll 86b.

As in the case with the embodiment of FIGS. 1–8, the anvil rollers 92 of both roller assemblies 101 and 103 are driven by a stepper motor-drive and the cutting rollers 86a and b are driven by a direct gear connection to its respective anvil roller 92.

Figure 12:
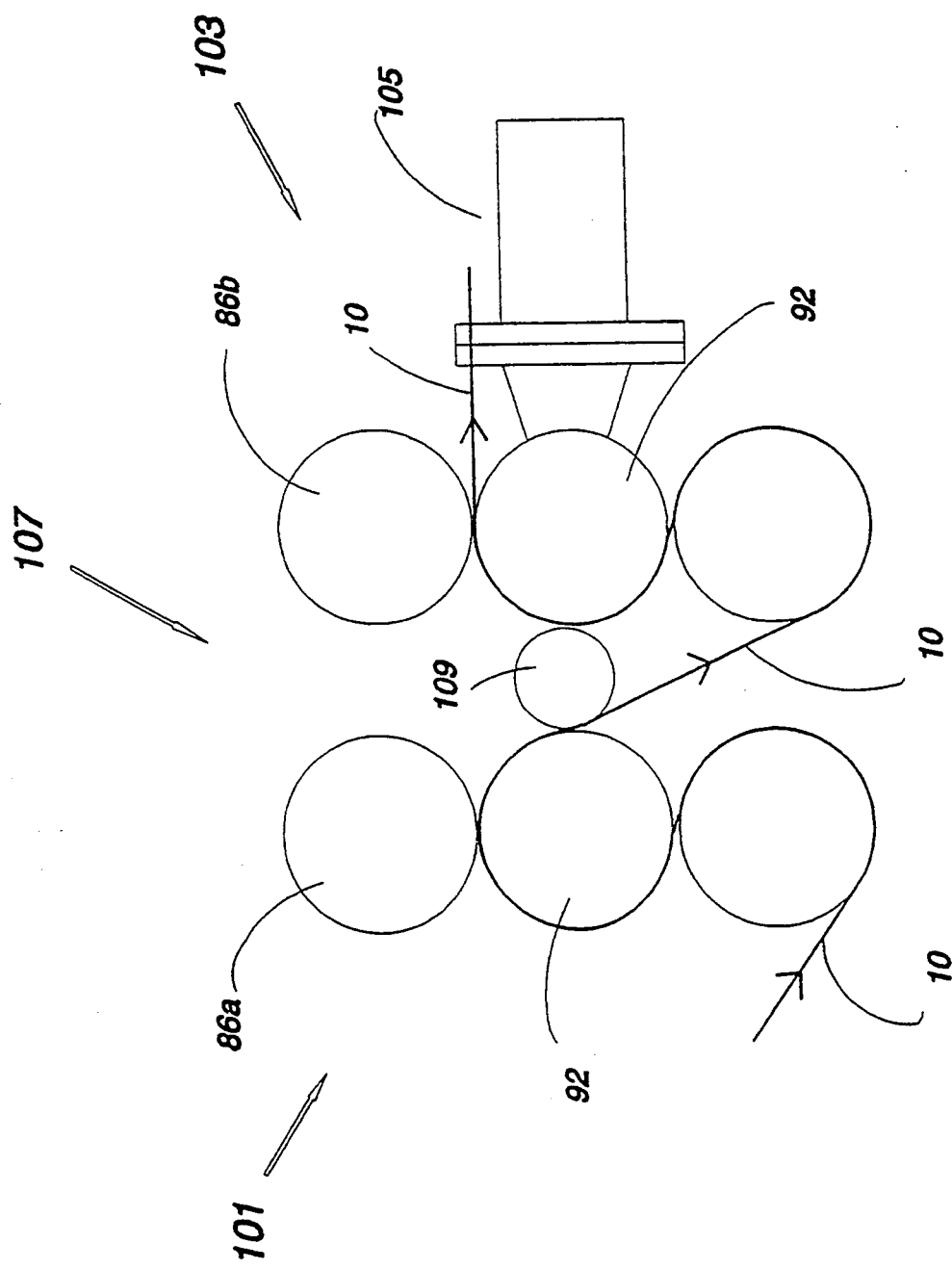
FIG. 12 schematically illustrates a drive gear arrangement in accordance with the embodiment of FIGS. 9-11.

FIG. 12 schematically illustrates the gear drive arrangement 107 in accordance with the embodiment of FIGS. 9–11. As shown therein, a gear drive motor 105 directly drives the anvil roller 92 of assembly 103. The anvil roller 92 has a gear at one end which directly meshes with a gear (not shown) at a like end of cutting roller 86b to drive the cutting roller 86b.

An intermediate gear 109 is also meshed with the gear (not shown) of the first anvil roller 92 of asembly 103 and also meshes with a gear (not shown) of anvil roller 92 of assembly 101. The gear of anvil roller 92 of assembly 101 likewise then meshes with a gear (not shown) of cutting roller 86a.

The arrangement of gears serves to drive the web 10 in a manner as previously described.

In this arrangement as shown in FIG. 9, the nip rollers 96 are adjustable upwardly and downwardly to adjust tension on the web 10. The nip rollers 96 are movable upwardly to nip the laminate web 10 between the nip roller 96 and anvil roller 92 thereby ensuring that the amount of laminate web 10 fed is equal in length to the surface of the anvil rollers 92 and supported fully thereby without separating from the anvil rollers 92. Accordingly, feeding of the web 10 is controlled to prevent it from building behind the nip to be passed uniformly between anvil rollers 92 and respective cutting rollers 86a and 86b.

In the case of the alternate embodiment of FIGS. 9–11, all components of the roller assemblies 101 and 103 are essentially the same as for the embodiments of FIGS. 1–8 except that the cutting edges 32 and 34 are now separated and scoring and cutting are done sequentially as opposed to simultaneously for FIGS. 1–8.

While the invention has been described in connection with a preferred embodiment, it will be understood that there is no intention to thereby limit the invention. On the contrary, there is intended to be covered all alternatives, modifications and equivalents as may be included within the spirit and scope of the invention as defined by the appended claims, which are the sole definition of the invention.

What is claimed is:

1. An apparatus for forming a transdermal drug delivery device from a multilayer web having layer of a backing material, a drug-containing pressure sensitive adhesive, and a release liner comprising at least one combination of:

an anvil roller supported in a manner for rotating about its axis;

a cutting roller having a cylindrical surface and supported for rotating about its axis, which axis is coplanar with the axis of the anvil roller, and said cutting roller being positionable in proximity to said anvil roller;

at least one cutting section fixedly mounted on and projecting above said surface, and having at least one cutting edge extending outwardly a predetermined distance from said surface and configured as a predetermined shape for defining a region on said surface for conducting at least one of scoring or cutting only said release liner and of cutting completely through said multilayer web as it is passed between said anvil roller and said cutting roller;

a nip roller rotatably mounted in proximity to the anvil roller, for, in cooperation with said anvil roller, urging said multilayer web along the surface of said anvil roller toward the cutting roller at a substantially same linear speed as a surface speed of said anvil roller and cutting roller; and drive means for counter-rotating the anvil roller and cutting roller at a substantially same surface speed for urging the multilayer web between the anvil roller and cutting roller such that, progressively along a line coplanar with the axes of the anvil roller and cutting roller, the cutting edge communicates with and at least one of scores or cuts only the releasable liner and of cuts completely through said multilayer web.

2. The apparatus of claim 1 in combination with an additional apparatus including an anvil roller; a cutting roller; a nip roller; drive means; and an additional cutting section configured for cutting completely through said multilayer web arranged on said cutting roller of said additional apparatus, said at least one cutting section comprising a first cutting section configured for scoring or cutting said release liner arranged on said cutting roller of said apparatus; and said apparatus and additional apparatus arranged with respect to said web to pass said web first through said apparatus for scoring or cutting and then through said additional apparatus for cutting completely through the web.

3. The apparatus of claim 1 which further comprise bearing means to support a shaft concentric with the axis of the anvil roller.

4. The apparatus of claim 1 which further comprises bearing means to support a shaft concentric with the axis of the cutting roller.

5. The apparatus of claim 4 further comprising:

a frame in which said cutting roller, anvil roller and nip roller are mounted;

pressure applying means comprising a pressure roller rotatably mounted in the frame and having pressure journals at either end, and means for exerting force against the pressure roller to be indirectly exerted on the cutting roller; and complimentary pressure journals on the cutting roller to rotationally communicate with the pressure roller journals.

6. The apparatus of claim 5 in which the bearing means is slidable with respect to the frame.

7. The apparatus of claim 5 which further comprises bearing means to support a shaft concentric with the pressure roller journals.

8. The apparatus of claim 5 in which the means to exert force on the pressure roller is a threaded pressure applicator, which threaded pressure applicator cooperates with a threaded hole in the frame.

9. The apparatus of claim 8 in which the threaded pressure applicator causes movement of the pressure roller by sliding its bearings with respect to the frame, thereby applying pressure through the pressure roller journals and complementary pressure journals to the cutting roller.

10. The apparatus of claim 9 which further comprises pressure measuring devices attached to the frame to permit reproducibility of the positioning and pressure of the cutting roller is proximity to the anvil roller.

11. The apparatus of claim 9 in which the bearing means of the cutting roller is slidable with respect to the frame and pressure applied to the cutting roller from its pressure journals in part positions of the cutting roller in proximity to the anvil roller.

12. The apparatus of claim 1 which further comprises:

pressure applying means for selectively exerting force against the cutting roller.

13. The apparatus of claim 1 which further comprises a positive drive connection between the cutting roller and the anvil roller to achieve said substantially same surface speed.

14. The apparatus of claim 13 in which the positive drive connection is meshing spur gears on the anvil roller and cutting roller.

15. The apparatus of claim 1 which further comprises a transfer plate disposed in close proximity to the anvil roller and cutting roller to receive the transdermal drug delivery devices and scrap remains of the web from which the said devices were cut and scored.

16. The apparatus of claim 15 in which cutting sections are positioned on the cutting roller in a close packed pattern to minimize scrap losses from the web.

17. The apparatus of claim 1 in which the cutting roller is sized with a diameter to achieve a repeat length when rotating that minimizes scrap losses from the web.

18. The apparatus of claim 1 which further comprises a field of resilient material attached to the cutting roller in proximity to but not touching the at least one cutting edge.

19. The apparatus of claim 1, wherein said at least one cutting section has a first cutting edge extending outwardly a first predetermined distance from the surface for cutting completely through the multilayer web and configured as a closed loop for defining a region on said surface, and a second cutting edge extending outwardly from said surface a second predetermined distance, said second predetermined distance being less than said first predetermined distance for scoring or cutting only the release liner, and said second cutting edge dividing said region to form two sub-regions thereof.

20. The apparatus of claim 19, wherein the two subregions are symmetrical.

21. An apparatus for forming a transdermal drug delivery device from a multilayer web having layers of a backing material, a drug-containing pressure sensitive adhesive, and a release liner comprising at least one combination of:

a frame;

an anvil roller mounted in the frame to rotate about its axis;

a cutting roller having a cylindrical surface mounted in the frame to rotate about its axis, which axis is coplanar with the axis of the anvil roller;

at least one cutting section fixedly mounted on and projecting about said surface having at least one cutting edge extending outwardly a first predetermined distance from the surface and configured as a predetermined shape for defining a region on said surface for conducting at least one of scoring or cutting only said release liner and of cutting completely through said multilayer web as it is passed between said anvil roller and said cutting roller;

means to position the cutting roller in proximity to the anvil roller;

a pressure applying means for selectively exerting force against the cutting roller to achieve said at least one of scoring and of cutting;

a resiliently covered nip roller rotatably mounted in the frame in proximity to the anvil roller which nip roller rotation is caused by at least one of contact with the multilayer web and pressure communicated from the anvil roller, which nip roller in cooperation with the anvil roller urges the multilayer web toward the cutting roller at substantially a same linear speed as a surface speed of the cutting roller and anvil roller; and a drive means to counter-rotate the anvil roller and the cutting roller to urge the multilayer web between these rollers such that, progressively along a line coplanar with the axes of these rollers.

22. The apparatus of claim 21 in combination with an additional apparatus including an anvil roller; a cutting roller; means to position the cutting roller; pressure applying means; resiliently covered nip rollers and drive means; and an additional cutting section configured for cutting completely through said multilayer web arranged on said cutting roller of said additional apparatus, said at least one cutting section comprising a first cutting section configured for scoring or cutting said release liner arranged on said cutting roller of said apparatus; and said apparatus and additional apparatus arranged with respect to said web to pass said web first through said apparatus for scoring or cutting and then through said second apparatus for cutting completely through the web.

23. The apparatus of claim 22 which further comprises bearing means to support a respective shaft concentric with the axis of each of the cutting roller.

24. The apparatus of claim 21 wherein said pressure applying means comprises a pressure roller rotatably mounted in the frame and having pressure journals at either end, and means for exerting force against the pressure roller to be indirectly exerted on the cutting roller, and complimentary pressure journals on the cutting roller to rotationally communicate with the pressure roller journals.

25. The apparatus of claim 24 in which the means to exert force on the pressure roller is a threaded pressure applicator, which threaded pressure applicator cooperates with a threaded hole in the frame.

26. The apparatus of claim 25 in which the threaded pressure applicator causes movement of the pressure roller by sliding its bearings with respect to the frame, thereby applying pressure through the pressure roller journals and complimentary pressure journals to the cutting roller.

27. The apparatus of claim 26 in which the bearing means of the cutting roller is slidable with respect to the frame and pressure applied to the cutting roller from its pressure journals in part positions the cutting roller in proximity to the anvil roller.

28. The apparatus of claim 27 which further comprises pressure measuring devices attached to the frame to permit reproducibility of the positioning and pressure of the cutting roller in proximity to the anvil roller.

29. The apparatus of claim 21 which further comprises a positive drive connection between the cutting roller and the anvil roller to achieve substantially identical surface speeds.

30. The apparatus of claim 29 in which the positive drive connection is meshing spur gears on the anvil roller and cutting roller.

31. The apparatus of claim 21 which further comprises a transfer plate disposed in close proximity to the anvil roller and cutting roller to receive the transdermal drug delivery devices and scrap remains of the web from which the said devices were cut and scored.

32. The apparatus of claim 21 in which the cutting roller is sized with a diameter to achieve a repeat length when rotating that minimizes scrap losses from the web.

33. The apparatus of claim 32 in which cutting sections are positioned on the cutting roller in a close packed pattern to minimize scrap losses from the web.

34. The apparatus of claim 21 which further comprises a field of resilient material attached to the cutting roller in proximity to but not touching said at least one cutting edge.

35. The apparatus of claim 21, wherein said at least one cutting section has a first cutting edge extending outwardly a first predetermined distance from the surface for cutting completely through the multilayer web and configured as a closed loop for defining a region on said surface, and a second cutting edge extending outwardly from said surface a second predetermined distance, said second predetermined distance being less than said first predetermined distance for scoring or cutting only the release liner, and said second cutting edge dividing said region to form two sub-regions thereof.

36. The apparatus of claim 35, wherein the two subregions are symmetrical.

37. The apparatus of claim 21 which further comprises bearing means to support a shaft concentric with the axis of the anvil roller.

38. An apparatus for forming a transdermal drug delivery device from a multilayer web having layers of a backing material, a drug-containing pressure sensitive adhesive, and a release liner, comprising:

an anvil roller supported in a manner for rotating about its axis;

a cutting roller having a cylindrical surface and supported for rotating about its axis, which axis is coplanar with the axis of the anvil roller, and said cutting roller being positionable in proximity to said anvil roller;

at least one cutting section fixedly mounted on and projecting above said surface, and having at least one cutting edge extending outwardly a predetermined distance from said surface and configured as a predetermined shape for defining a region on said surface for conducting at least one of scoring or cutting only said release liner and of cutting completely through said multilayer web as it is passed between said anvil roller and said cutting roller;

said anvil roller and cutting roller being counter rotatable in relation to each other, whereby counter rotation of said anvil roller and cutting rollers functions to urge the multilayer web between said cutting roller and anvil roller such that, progressively along a line coplanar with the axes of the rollers, such that at least one of the cutting edge communicates with and cuts through the multilayer web or the cutting edge communicates with and scores or cuts only the release liner occurs; and pressure applying means for selectively applying pressure to said anvil roller for causing said at least one of cutting and of scoring or cutting to occur.

39. The apparatus of claim 38 in combination with an additional apparatus including an anvil roller; a cutting roller; and pressure applying means; and an additional cutting section configured for cutting completely through said multilayer web arranged on said cutting roller of said additional apparatus; said at least one cutting section comprising a first cutting section configured for scoring or cutting said release liner arranged on said cutting roller of said apparatus and additional apparatus arranged with respect to said web to pass said web first through said apparatus for scoring or cutting and then through said additional apparatus for cutting completely through the web.

40. The apparatus of claim 38 wherein said pressure applying means comprises a pressure roller rotatably mounted and having pressure journals at either end, and means for exerting force against the pressure roller to be indirectly exerted on the cutting roller, and complimentary pressure journals on the cutting roller to rotationally communicate with the pressure roller journals.

41. The apparatus of claim 38 wherein said at least one cutting section comprises a first cutting edge extending outwardly or first predetermined distance from the surface for cutting completely through the multilayer web and configured as a closed loop for defining a region on said surface, and a second cutting edge extending outwardly from said surface a second predetermined distance, said second predetermined distance being less than said first predetermined distance for scoring only the release liner, and said second cutting edge dividing said region to form two sub-regions thereof.

42. The apparatus of claim 41, wherein the two subregions are symmetrical.

* * * * *